United States Patent
Soma et al.

(10) Patent No.: US 12,213,735 B2
(45) Date of Patent: Feb. 4, 2025

(54) EYE EXAMINATION ATTACHMENT, CONTROL DEVICE, AND OPHTHALMIC MICROSCOPE SYSTEM

(71) Applicant: SONY GROUP CORPORATION, Tokyo (JP)

(72) Inventors: Yoshio Soma, Tokyo (JP); Tomoyuki Ootsuki, Tokyo (JP); Junichiro Enoki, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 527 days.

(21) Appl. No.: 17/593,097

(22) PCT Filed: Mar. 12, 2020

(86) PCT No.: PCT/JP2020/010690
§ 371 (c)(1),
(2) Date: Sep. 9, 2021

(87) PCT Pub. No.: WO2020/195865
PCT Pub. Date: Oct. 1, 2020

(65) Prior Publication Data
US 2022/0175245 A1     Jun. 9, 2022

(30) Foreign Application Priority Data

Mar. 26, 2019   (JP) ................................ 2019-058159

(51) Int. Cl.
*A61B 3/13*     (2006.01)
*A61B 3/00*     (2006.01)
(Continued)

(52) U.S. Cl.
CPC .............. *A61B 3/13* (2013.01); *A61B 3/0041* (2013.01); *A61B 3/14* (2013.01); *G06T 5/80* (2024.01);
(Continued)

(58) Field of Classification Search
CPC ........... A61B 3/13; A61B 3/0041; A61B 3/14; A61B 3/0016; A61B 3/0075; A61B 3/08;
(Continued)

(56) References Cited

U.S. PATENT DOCUMENTS 5,216,456 A   6/1993  Volk
5,424,789 A   6/1995  Volk
(Continued)

FOREIGN PATENT DOCUMENTS

CA      2949393 A1    1/2016
JP    2004361891 A   12/2004
(Continued)

OTHER PUBLICATIONS

International Search Report and Written Opinion of PCT Application No. PCT/JP2020/010690, issued on May 26, 2020, 11 pages of ISRWO.

*Primary Examiner* — Mohammed A Hasan
(74) *Attorney, Agent, or Firm* — CHIP LAW GROUP

(57) ABSTRACT

Provided is an eye examination attachment that includes a joining unit, a front optical system, and a communication unit. The joining unit is capable of being joined to an ophthalmic microscope. The front optical system includes a front lens capable of being placed in front of an eye to be examined. The communication unit sends information regarding the front optical system to an external device.

21 Claims, 9 Drawing Sheets

(51) Int. Cl.
  *A61B 3/14* (2006.01)
  *G06T 5/80* (2024.01)
  *H04N 9/64* (2023.01)
  *H04N 13/296* (2018.01)

(52) U.S. Cl.
  CPC ... *H04N 9/646* (2013.01); *G06T 2207/10012* (2013.01); *G06T 2207/10024* (2013.01); *G06T 2207/10056* (2013.01); *G06T 2207/30041* (2013.01); *H04N 13/296* (2018.05)

(58) Field of Classification Search
  CPC ............ G06T 5/80; G06T 2207/10012; G06T 2207/10024; G06T 2207/10056; G06T 2207/30041; H04N 9/646; H04N 13/296; H04N 13/239; A61F 9/007
  USPC ........................................................ 351/206
  See application file for complete search history.

(56) References Cited

U.S. PATENT DOCUMENTS

| | | | |
|---|---|---|---|
| 2002/0159031 A1* | 10/2002 | Kanngiesser | A61B 3/125 351/219 |
| 2010/0290006 A1* | 11/2010 | Flanagan | A61B 5/163 351/205 |
| 2014/0358039 A1* | 12/2014 | Pearson | A61B 3/10 600/587 |
| 2016/0008169 A1 | 1/2016 | Yu | |
| 2018/0008140 A1 | 1/2018 | Izatt | |
| 2019/0038135 A1 | 2/2019 | Lee et al. | |
| 2019/0042698 A1* | 2/2019 | Pohl | G16H 40/63 |
| 2019/0076019 A1 | 3/2019 | Farberov | |
| 2020/0237210 A1* | 7/2020 | Limon | G01S 17/88 |

FOREIGN PATENT DOCUMENTS

| | | |
|---|---|---|
| JP | 2008-093433 A | 4/2008 |
| JP | 2015505685 A | 2/2015 |
| JP | 2017-124204 A | 7/2017 |
| JP | 2017-522112 A | 8/2017 |
| KR | 10-2017-0009996 A | 1/2017 |
| KR | 10-2017-0093645 A | 8/2017 |
| WO | 2017/135564 A1 | 8/2017 |

* cited by examiner

EYE EXAMINATION ATTACHMENT, CONTROL DEVICE, AND OPHTHALMIC MICROSCOPE SYSTEM

CROSS REFERENCE TO RELATED APPLICATIONS

This application is a U.S. National Phase of International Patent Application No. PCT/JP2020/010690 filed on Mar. 12, 2020, which claims priority benefit of Japanese Patent Application No. JP 2019-058159 filed in the Japan Patent Office on Mar. 26, 2019. Each of the above-referenced applications is hereby incorporated herein by reference in its entirety.

TECHNICAL FIELD

The present technology relates to an eye examination attachment, a control device, and an ophthalmic microscope system, which are used for ophthalmic surgery and the like.

BACKGROUND ART

In ophthalmic surgery, an eye examination attachment including a front lens is added and used to an ophthalmic surgical microscope in some cases. Wide-angle lenses in vitrectomy and gonioscopes in minimally invasive glaucoma surgery (MIGS) for treating an angle have been widely used as front lenses.

For example, an ophthalmic surgical microscope to which a wide-angle observation attachment including a wide-angle lens, which is an eye examination attachment is added, is suitable for observing a fundus in a wide range. An image of an eye to be examined, which is obtained via the wide-angle lens, is distorted due to the addition of the wide-angle observation attachment. Moreover, various optical conditions in the microscope change due to the addition of the wide-angle observation attachment.

According to Patent Literature 1, an image inverting system of a microscope is turned on by joining of an eye examination attachment.

CITATION LIST

Patent Literature

Patent Literature 1: Japanese Patent Application Laid-open No. 2008-93433

DISCLOSURE OF INVENTION

Technical Problem

It is desirable to provide a user of a microscope with an image of an eye to be examined that is suitable for observation when an eye examination attachment is added.

In view of the above-mentioned circumstances, it is an object of the present technology to provide an eye examination attachment, a control device, and an ophthalmic microscope system, by which an image of an eye to be examined that is suitable for observation can be provided.

Solution to Problem

In order to accomplish the above-mentioned object, an eye examination attachment according to an embodiment of the present technology includes a joining unit, a front optical system, and a communication unit.

The joining unit is capable of being joined to an ophthalmic microscope.

The front optical system includes a front lens capable of being placed in front of an eye to be examined.

The communication unit sends information regarding the front optical system to an external device.

With this configuration, the information regarding the front optical system of the eye examination attachment can be provided to the external device.

The eye examination attachment may further include a storage unit that stores optical characteristic information of the front optical system as the information regarding the front optical system.

The optical characteristic information of the front optical system may include at least one of functional characteristic information of the front lens, a shape of the front lens, or a material of the front lens.

The functional characteristic information may include at least one of a focal distance, a distortion coefficient, a refractive index, a wavelength characteristic, or a polarization characteristic of the front lens.

The eye examination attachment may further include a state information acquisition unit that acquires state information of the optical system as the information regarding the front optical system.

The state information of the front optical system may include position information of the front lens.

The front optical system may include the front lens and an intermediate lens that is placed between the front lens and the ophthalmic microscope, and the state information of the front optical system may further include at least one of position information of the intermediate lens or distance information between the intermediate lens and the front lens.

The front lens may be configured to be replaceable, and the storage unit may be configured such that the optical characteristic information of the front optical system is writable on the storage unit.

The eye examination attachment may further include a front optical system control unit that controls the front optical system on the basis of a control signal from the external device.

In order to accomplish the above-mentioned object, a control device according to an embodiment of the present technology includes a communication unit.

The communication unit receives information regarding a front optical system of an eye examination attachment including the front optical system including a front lens capable of being placed in front of an eye to be examined.

The control device may further include: an image acquisition unit that acquires a captured image of an eye to be examined in front of which the front lens is placed; and an image generating unit that generates a display image by performing image processing on the captured image with the information regarding the front optical system.

The eye examination attachment may further include a storage unit that stores optical characteristic information of the front optical system as the information regarding the front optical system.

The information regarding the front optical system may include a distortion coefficient of the front lens, and the image generating unit may generate the display image by performing distortion correction on the captured image with the distortion coefficient.

The information regarding the front optical system may include a material of the front lens, and the image generating unit may generate the display image by controlling a maximum magnification on the basis of the material of the lens.

The control device information regarding the front optical system may include a polarization characteristic of the front lens, and the image generating unit may generate the display image by performing specular reflection removal on the captured image on the basis of the polarization characteristic of the front lens.

The information regarding the front optical system may include a shape of the front lens, and the image generating unit may generate the display image by performing color aberration correction on the captured image with shape information of the front lens.

The captured image may be a stereo image, the information regarding the front optical system may include a focal distance of the front lens, and the image generating unit may generate the display image by controlling a parallax of the stereo image with the focal distance of the front lens.

The eye examination attachment may be configured to be capable of being joined to an ophthalmic microscope including an observation optical system, and the control device may further include a microscope control signal generating unit that generates a control signal for controlling at least one of the observation optical system or the front optical system, using the information regarding the front optical system.

In order to accomplish the above-mentioned object, an ophthalmic microscope system according to an embodiment of the present technology includes an ophthalmic microscope, an eye examination attachment, and a control device.

The eye examination attachment includes a joining unit that is joined to the ophthalmic microscope, a front optical system including a front lens capable of being placed in front of an eye to be examined, and a communication unit that sends information regarding the front optical system.

The control device includes a communication unit that receives the information regarding the front optical system.

The ophthalmic microscope may further include an image pickup element, and the control device may further include an image acquisition unit that acquires a captured image of an eye to be examined in front of which the front lens is placed, the eye to be examined being imaged by the image pickup element, and an image generating unit that generates a display image by performing image processing on the captured image with the information regarding the front optical system.

The ophthalmic microscope may further include an observation optical system, and the control device may further include a microscope control signal generating unit that generates a control signal for controlling at least one of the observation optical system or the front optical system, using the information regarding the front optical system.

MODE(S) FOR CARRYING OUT THE INVENTION

An ophthalmic microscope system according to an embodiment of the present technology will be described. Here, the description will be given taking an example in which vitrectomy is performed by using an ophthalmic microscope in which a wide-angle observation attachment is joined to a microscope as an eye examination attachment, the wide-angle observation attachment including a front optical system including a wide-angle lens (front lens).

In this embodiment, an example in which the present technology is applied to a heads up surgery (HUS) system that enables a user of the ophthalmic microscope, such as an ophthalmologist and an assistant, to perform observation and surgery while viewing on a display device an image captured by an image pickup element instead of looking through the microscope will be described. A display image is displayed on the display device. The display image is obtained by performing processing on a captured image captured by the image pickup element provided in the microscope and is an operative field image.

The eye examination attachment has information regarding the front optical system. In the ophthalmic microscope system according to this embodiment, image processing is performed on a captured image by using optical characteristic information of the front optical system that is the information regarding the front optical system.

Moreover, the eye examination attachment includes a state information acquisition unit that acquires state information of the front optical system. In the ophthalmic microscope system according to this embodiment, the optical system of the microscope is controlled by using the state information of the front optical system that is the information regarding the front optical system.

[Configuration of Ophthalmic Microscope System]

Figure 1:
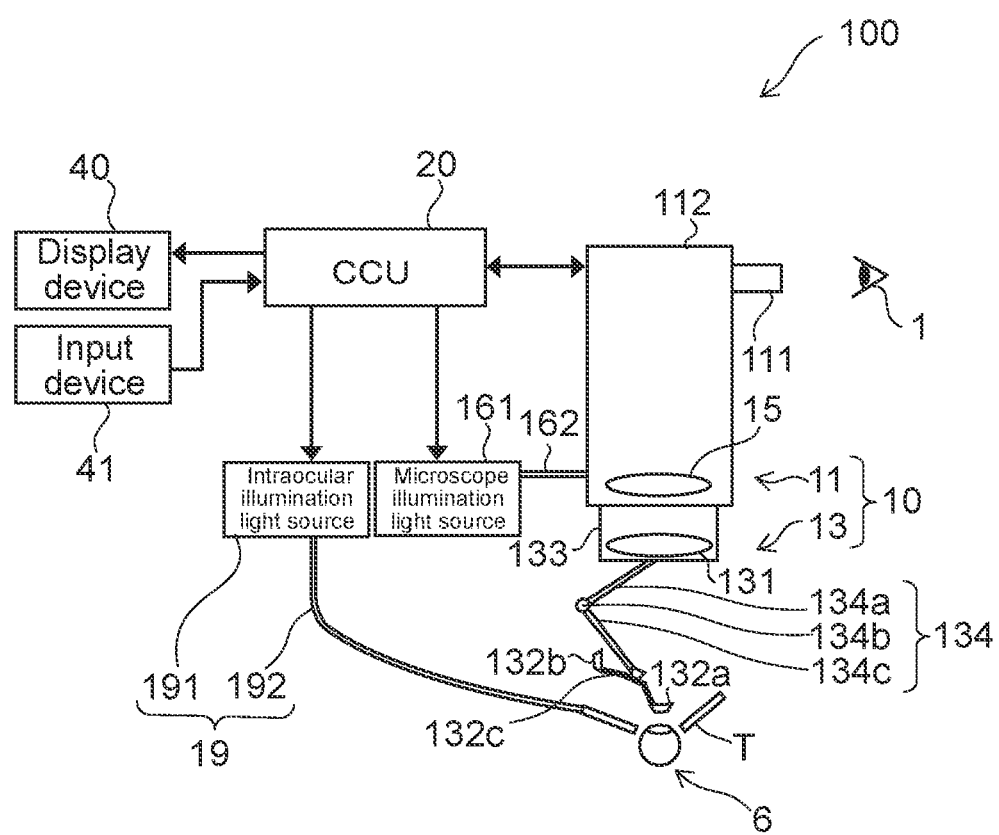
FIG. 1 A schematic diagram of an ophthalmic microscope system according to an embodiment of the present technology.

FIG. 1 is a schematic diagram showing a configuration of an ophthalmic microscope system 100 (hereinafter, referred to as microscope system) according to this embodiment.

As shown in FIG. 1, the microscope system 100 includes an ophthalmic microscope 10 with the eye examination attachment (hereinafter, referred to as microscope with attachment), a camera control unit 20 (hereinafter, referred to as CCU) serving as a control device, a display device 40, and an input device 41.

The microscope 10 with the attachment is used by a user of the microscope system 100 for observing a magnified image of an eye to be examined 6 in an examination or surgery in the ophthalmologic field. In the figure, the reference sign 1 denotes an eye of the user of the microscope 10 with the attachment. The user can perform an examination or surgery while viewing a display image displayed on the display device 40. The eye to be examined 6 is a patient's eye on which an examination or surgery is to be performed.

The microscope 10 with the attachment includes an ophthalmic microscope 11 (hereinafter, referred to as microscope) and an eye examination attachment 13.

The microscope 11 includes a tube main body 112 having observation tubes 111, a microscope illumination light source 161 serving as an extraocular illumination light source, and an intraocular illuminator 19.

The microscope 11 may be an optical microscope having a general configuration. Two observation tubes 111 are provided for both the left and right eyes, though not limited thereto.

The details of the microscope 10 with the attachment will be described later.

The CCU 20 generates a display image by performing image processing on a captured image acquired by an image pickup element 181 mounted in the microscope 11, which will be described later, with information of a front optical system 130 of the eye examination attachment 13, which will be also described later.

The details of the CCU 20 will be described later.

The display device 40 displays a display image formed by image processing performed in the CCU 20 on the basis of the captured image acquired by the image pickup element 181. The display device 40 is a generally-used display or a head-mounted display. Alternatively, the display device 40 may be a plurality of displays. The plurality of displays can be a display for a surgeon and a display for an assistant, for example.

The input device 41 is an input interface to the microscope system 100. The user can input body information of a patient, various types of information regarding the surgery, and the like through the input device 41. Moreover, for example, the user can input an instruction to change various settings related to the microscope in accordance with the situation, and the like through the input device 41.

The type of input device 41 is not limited, and the input device 41 may be any type of well-known input devices. A mouse, a keyboard, a touch panel, a switch, a foot switch, a lever, or the like can be applied as the input device 41, for example. In a case where the touch panel is used as the input device 41, the touch panel may be provided on the display surface of the display device 40.

Additionally, the input device 41 may include a microphone capable of collecting the user's voice and various inputs may be performed by voice through the microphone. Such a configuration of the input device 41 to be capable of inputting various types of information in a contactless manner enables the user belonging to a particularly clean area to operate the device belonging to a non-clean area in a contactless manner. The user can also operate the device without releasing the hand from the surgical instrument that the user holds, which improves the convenience of the user.

Figure 4:
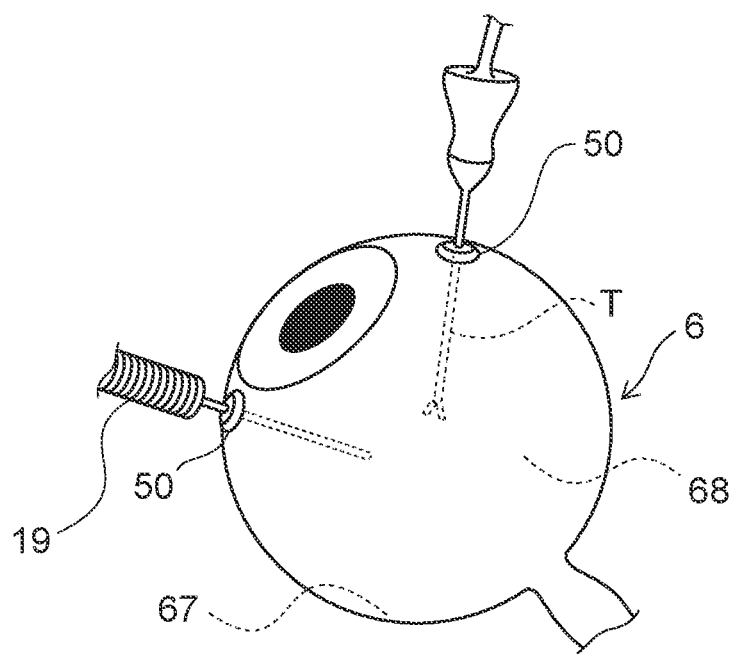
FIG. 4 A schematic diagram showing a state of surgery of an eye that is an observation target of the ophthalmic microscope system.
Figure 5:
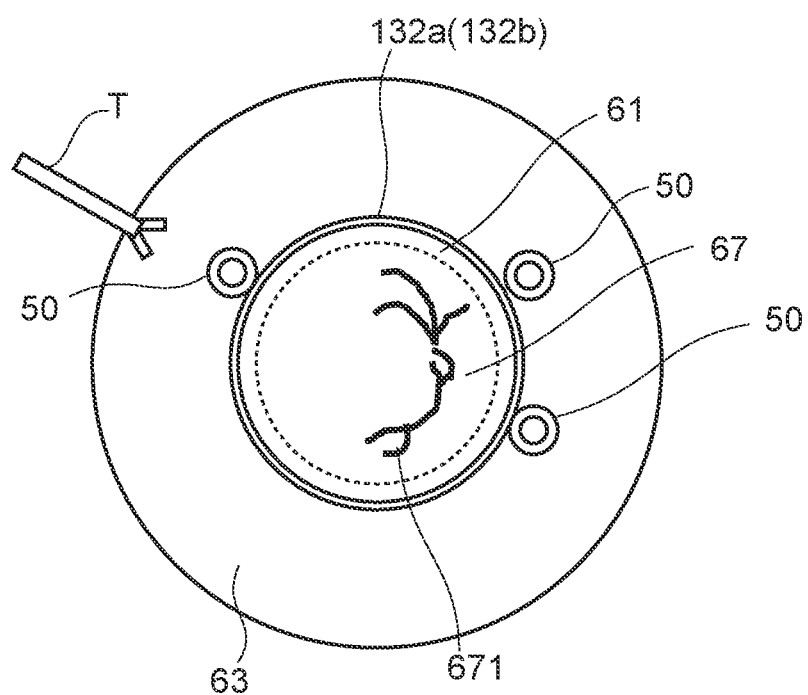
FIG. 5 A schematic diagram showing a state of the surgery of the eye that is the observation target of the ophthalmic microscope system and a plan view as the eye in front of which a front lens is placed is viewed from the front side.

FIGS. 4 and 5 are schematic diagrams showing a state of the vitrectomy in the microscope system 100. FIGS. 4 and 5 show a surgical instrument T used for surgery of an eye. FIG. 4 is a schematic perspective view of an eyeball of the eye to be examined 6. FIG. 4 shows a state in which the intraocular illuminator 19 and the surgical instrument T are inserted into the eye. The front lens is not shown in FIG. 4. FIG. 5 is a diagram as the eye to be examined 6 in front of which a wide-angle lens 132*a* or a magnifying lens 132*b* as the front lens is placed is viewed from in a front direction. FIG. 5 shows a state before the intraocular illuminator 19 and the surgical instrument T are inserted.

Figure 6:
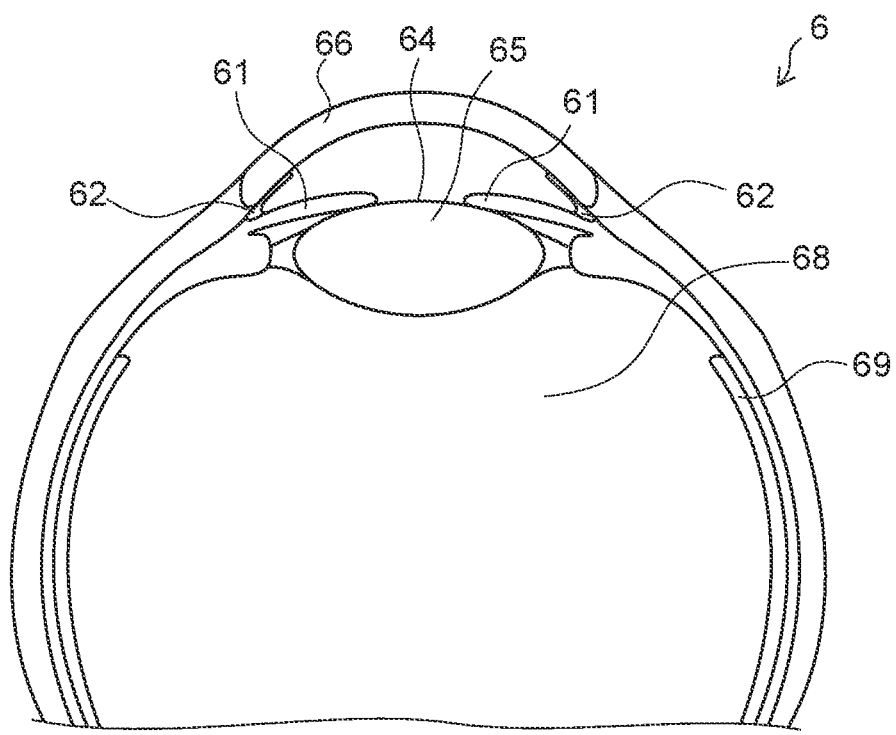
FIG. 6 A cross-sectional view of the eye.

FIG. 6 is a partial cross-sectional view of the eye to be examined 6.

An instrument suitable for a treatment at that time is used as for the surgical instrument T. For example, the surgical instrument T may be a vitreous cutter, forceps, a backflush needle, internal limiting membrane (ILM) forceps, a laser device for retinal laser photocoagulation, or the like.

As shown in FIGS. 5 and 6, the eye to be examined 6 includes parts such as an iris 61, a crystalline lens 65, and a cornea 66. On the surface of the crystalline lens 65, a pupil 64 is located in the middle of the iris 61 and an angle 62 is located at the periphery of the cornea 66. A vitreous body 68 is a gel-like substance that occupies a large portion of the eyeball behind the crystalline lens 65 in front of a retina 69. In FIG. 5, the reference sign 671 denotes a blood vessel of a fundus 67.

Since it is necessary to observe the fundus 67 in the vitrectomy, the intraocular illuminator 19 is, as shown in FIG. 4, inserted into the eye to be examined 6, intraocular illumination is performed, and then the surgical instrument T is inserted into the eye for performing the surgery. The intraocular illuminator 19, a vitreous cutter for resecting and absorbing the vitreous body, and a tubular trocar 50 serving as a guide for guiding and withdrawing a tube (not shown) for injecting a perfusate for maintaining the eyeball shape during the surgery are placed on the eye to be examined 6.

As shown in FIG. 5, the wide-angle lens 132*a* (or the magnifying lens 132*b*) is provided to correspond to the cornea when the wide-angle lens 132*a* (or the magnifying lens 132*b*) is placed in front of the eye to be examined 6. In a wide-angle observation using the wide-angle lens 132*a*, the pupil 64 is observed in a state in which it is very close to the edge of the wide-angle lens 132*a* (or the magnifying lens 132*b*) in order to observe the fundus 67.

[Configuration of Ophthalmic Microscope with Eye Examination Attachment]

Next, the microscope 10 with the attachment will be described.

Figure 2:
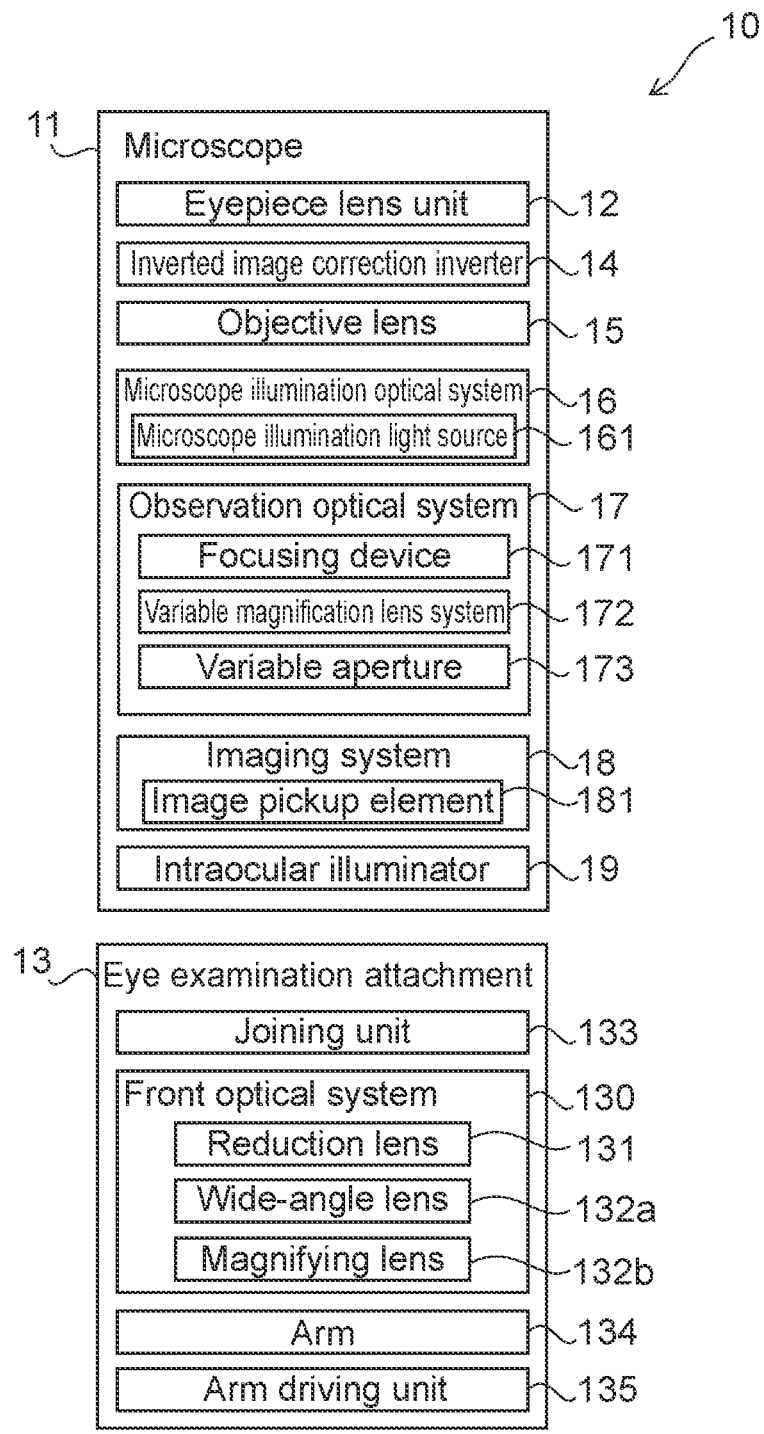
FIG. 2 A configuration block diagram showing a configuration of an ophthalmic microscope that constitutes a part of the ophthalmic microscope system.

FIG. 2 is a configuration block diagram showing a configuration of the microscope 10 with the attachment shown in FIG. 1.

As shown in FIG. 2, the microscope 10 with the attachment includes the microscope 11 and the eye examination attachment 13.

(Configuration of Ophthalmic Microscope)

The microscope 11 includes an eyepiece lens unit 12, an inverted image correction inverter 14, an objective lens 15, a microscope illumination optical system 16, an observation optical system 17, an imaging system 18, and the intraocular illuminator 19.

The eyepiece lens unit 12 further magnifies the image produced by the observation optical system 17 in order to observe the image with the eyes. The user can perform an eyepiece observation on an image transmitted through the eyepiece lens unit 12, through the observation tubes 111. Hereinafter, the image to be observed in the eyepiece observation will be referred to as an observation image.

The tube main body 112 houses the inverted image correction inverter 14, the objective lens 15, a part of the microscope illumination optical system 16, the observation optical system 17, and the imaging system 18.

The inverted image correction inverter 14 performs inversion processing of returning the inverted image to the normal image through the wide-angle lens 132a (or the magnifying lens 132b).

The ON/OFF of the inverted image correction inverter 14 is controlled on the basis of a detection result of joining between the microscope 11 and the eye examination attachment 13, for example.

The microscope illumination optical system 16 illuminates the eye to be examined 6 through the objective lens 15.

The microscope illumination optical system 16 is divided into a microscope illumination optical system for the user's left eye and a microscope illumination optical system for the user's right eye. In the following description, the microscope illumination optical system will be referred to as the microscope illumination optical system 16 unless it is particularly necessary to distinguish between the microscope illumination optical system for the right eye and the microscope illumination optical system for the left eye.

As shown in FIGS. 1 and 2, the microscope illumination optical system 16 includes the microscope illumination light source 161 and an optical fiber 162, which are placed outside the tube main body 112, and a condenser lens, a collimating lens, and a reflection mirror, which are housed in the tube main body 112 and not shown in the figures.

The microscope illumination light source 161 emits illumination light for illuminating the eye to be examined 6 from the outside of the eye to be examined 6 during an examination, surgery, or the like.

One end of the optical fiber 162 is connected to the microscope illumination light source 161 and the other end of the optical fiber 162 is connected to the tube main body 112.

The illumination light output (extraocular illumination light) from the microscope illumination light source 161 is guided by the optical fiber 162, enters the condenser lens, and becomes a parallel light beam through the collimating lens. The parallel light beam is reflected by the reflection mirror toward the objective lens 15, passes through the objective lens 15, and is radiated to the eye to be examined 6. The illumination light radiated to the eye to be examined 6 is reflected and scattered by parts of the eye to be examined 6, such as the cornea 66 and the retina 69.

The reflected and scattered return light passes through the objective lens 15 and enters the observation optical system 17 when the eye examination attachment 13 is not located on the observation optical path. On the other hand, when the eye examination attachment 13 is located on the observation optical path, the return light passes through the wide-angle lens 132a (or the magnifying lens 132b) and a reduction lens 131 serving as an intermediate lens, which will be described later, and the objective lens 15 and enters the observation optical system 17.

The intraocular illuminator 19 is provided outside the tube main body 112 and illuminates the inside of the eye to be examined 6.

The intraocular illuminator 19 includes an intraocular illumination light source 191 and an optical fiber 192.

The intraocular illumination light source 191 emits illumination light (intraocular illumination light) for irradiating the inside of the eye to be examined 6 for vitrectomy or the like in which it is necessary to observe a fundus in a wide range.

One end of the optical fiber 192 can be connected to the intraocular illumination light source 191 and the other end of the optical fiber 192 can be inserted into the eye to be examined 6.

As shown in FIG. 4, in a case of observing the fundus 67 of the eye to be examined 6, the illumination light output from the intraocular illumination light source 191 is guided by the optical fiber 192 and is emitted into the eye to be examined 6 from the other end of the optical fiber 192.

As shown in FIG. 2, the observation optical system 17 is for observing, through the objective lens 15, the eye to be examined 6 illuminated by the microscope illumination optical system 16 and the intraocular illuminator 19. The observation optical system 17 transmits a projected image of the eye to be examined 6 to the eye 1 of the user or to the image pickup element 181 to be described later.

In the microscope 10 with the attachment in a state in which the eye examination attachment 13 is joined, return light (the image of the eye to be examined) reflected and scattered by parts of the eye to be examined 6 is formed as an image on the image pickup element 181 or enters the eyepiece lens unit 12 via the front optical system 130 of the eye examination attachment 13 to be described later, the objective lens 15, and the observation optical system 17.

More specifically, the return light transmits the wide-angle lens 132a (or the magnifying lens 132b), the reduction lens 131 serving as the intermediate lens, the objective lens 15, and the observation optical system 17 and is formed as an image on the image pickup element 181 or enters the eyepiece lens unit 12.

On the other hand, in the microscope 10 with the attachment in a state in which the eye examination attachment 13 is not joined, the return light (the image of the eye to be examined) from the eye to be examined 6 is formed as an image on the image pickup element 181 or enters the eyepiece lens unit 12 via the objective lens 15 and the observation optical system 17.

The observation optical system 17 is divided into an observation optical system for the user's left eye and an observation optical system for the user's right eye and has respective observation optical paths for the observation optical systems. The observation optical system will be referred to as the observation optical system 17 unless it is particularly necessary to distinguish between the observation optical system for the right eye and the observation optical system for the left eye.

The observation optical system 17 includes a focusing device 171, a variable magnification lens system 172 including a plurality of zoom lenses, an imaging lens (not shown), a variable aperture 173, a beam splitter (not shown).

The focusing device 171 is capable of moving up and down the microscope 10 with the attachment. Accordingly, the operation interval between the objective lens 15 and the patient's eye to be examined 6 can be adjusted, and the microscope 10 with the attachment is focused on a region to be examined of the eye to be examined 6. Therefore, the control on the focusing device 171 can control the focal position of the optical system through which the return light (the image of the eye to be examined) passes before the return light (the image of the eye to be examined) from the eye to be examined 6 is formed as an image on the image pickup element 181.

The plurality of zoom lenses of the variable magnification lens system 172 is movable along the optical axis of the observation optical system. The movement of the plurality of zoom lenses changes the magnification in the captured image of the eye to be examined 6. Therefore, the control on the variable magnification lens system 172 can control the magnification of the optical system through which the return light (the image of the eye to be examined) passes before the return light (the image of the eye to be examined) from the eye to be examined 6 is formed as an image on the image pickup element 181, and can control the captured image, the angle of view of the display image, and the angle of view of the observation image.

The depth of field of the optical system through which the return light (the image of the eye to be examined) passes before the return light (the image of the eye to be examined) from the eye to be examined 6 is formed as an image on the image pickup element 181 depends on focal length and F-value of the lens and an imaging distance. Therefore, the control on the focusing device 171 and the variable aperture 173 can control the depth of field of the optical system through which the return light (the image of the eye to be examined) passes before the return light (the image of the eye to be examined) from the eye to be examined 6 is formed as an image on the image pickup element 181.

The return light entering the observation optical system 17 is controlled in terms of the magnification by the variable magnification lens system 172, passes through the imaging lens and the variable aperture 173, and enters the beam splitter. The beam splitter guides part of the return light to the imaging system 18 and guides the other part of the return light to the eyepiece lens unit 12. The eyepiece observation can be performed by the return light entering the eyepiece lens unit 12.

The imaging system 18 includes the imaging lens (not shown), the image pickup element 181, and the like. The image pickup element 181 includes, for example, an image sensor such as a charge coupled device (CCD) and a complementary metal oxide semiconductor (CMOS) and the like. The light receiving surface of the image pickup element 181 is placed at a position optically conjugate with the focal position of the objective lens 15.

The imaging system 18 may be associated with both the left and right observation optical systems 17 or may be associated with one of the left and right observation optical systems 17. In a case where the imaging system 18 corresponds to the left and right observation optical systems 17, two image pickup elements 181 are provided, and thus a captured image that is a stereo image can be obtained.

The image pickup elements 181 are mounted on the microscope 10 with the attachment and capable of imaging the eye to be examined 6 through the front optical system 130 and the observation optical system 17. The captured image captured by the image pickup element 181 is output to the CCU 20.

(Configuration of Eye Examination Attachment)

The eye examination attachment 13 is removably placed on the microscope 11.

As shown in FIG. 1, the eye examination attachment 13 is provided between the objective lens 15 and the eye to be examined 6.

As shown in FIGS. 1 and 2, the eye examination attachment 13 includes a joining unit 133, the front optical system 130, an arm 134, a holding plate 132c, and an arm driving unit 135.

The joining unit 133 is a portion in which the eye examination attachment 13 is detachably joined to the microscope 11. The attachment of the eye examination attachment 13 to the microscope 11 can be detected through electrical conduction at a contact point provided in a portion in which the eye examination attachment 13 and the microscope 11 are brought into contact with each other.

In this manner, the joining may be detected on the basis of whether or not electrical conduction is achieved. Alternatively, a switch for changing the joining state may be provided and the user may use the switch to switch between a state in which the eye examination attachment 13 and the microscope 11 are joined to each other and a state in which the eye examination attachment 13 and the microscope 11 are not joined to each other.

The front optical system 130 includes the reduction lens 131 and the wide-angle lens 132a and the magnifying lens 132b serving as the front lenses. In a case of observing the eye to be examined 6 through the front lens in the microscope 10 with the attachment, to which the eye examination attachment 13 is joined, the wide-angle lens 132a (or the magnifying lens 132b), the reduction lens 131, the objective lens 15, and the observation optical system 17 are located on the observation optical path.

The reduction lens 131 increases the refractive power of the objective lens 15.

Figure 7:
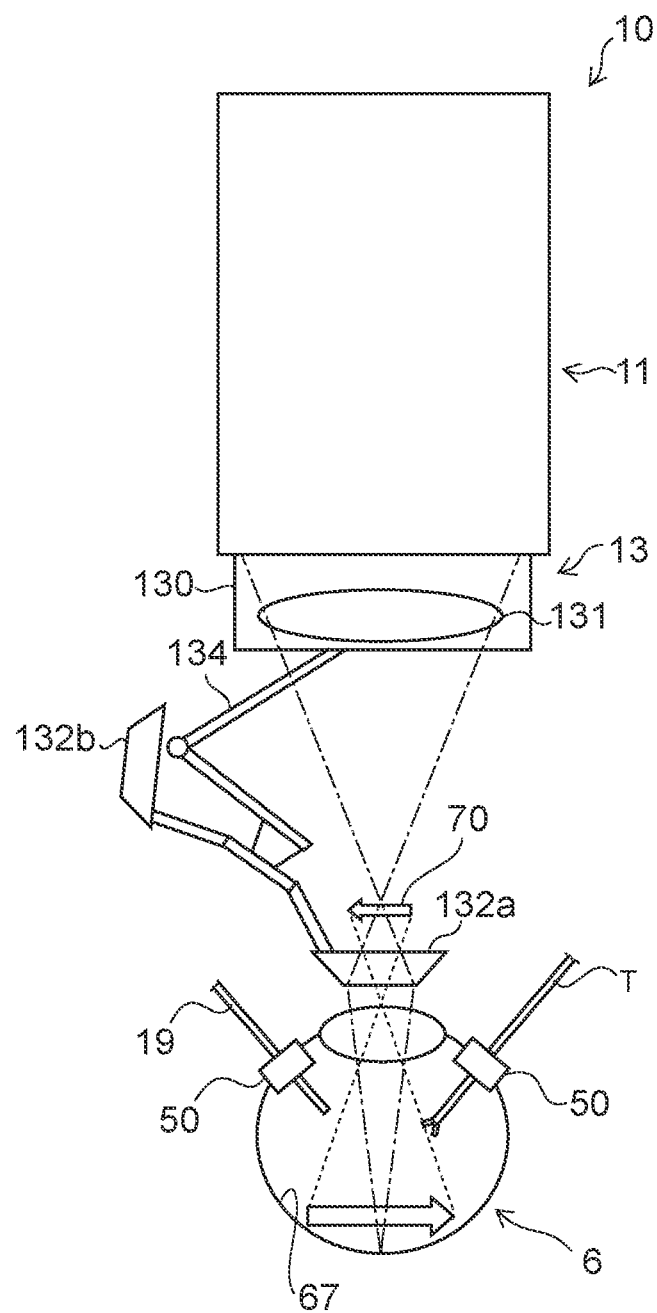
FIG. 7 A schematic diagram showing a state of the surgery of the eye using the ophthalmic microscope system.

FIG. 7 is a schematic diagram showing a state of eye surgery using the microscope 10 with the attachment, to which the eye examination attachment 13 is joined. FIG. 7 shows a state in which the wide-angle lens 132a is placed in front of the eye to be examined 6.

As shown in FIG. 7, the reduction lens 131 is made to coincide with an intermediate image plane 70 by displacing the focal plane of the observation optical path of the microscope 10 with the attachment.

The reduction lens 131 is not essential in some microscope optical systems. In a case where the wide-angle lens is used as the front lens, the eye examination attachment typically includes the reduction lens in addition to the wide-angle lens.

The wide-angle lens 132a enables the fundus 67 of the eye to be examined 6 to be observed. When the wide-angle lens 132a is placed on the observation optical path, the fundus 67 of the eye to be examined 6 can be observed.

As shown in FIG. 7, the wide-angle lens 132a causes an intermediate image in which the fundus 67 is inverted to be generated on the intermediate image plane 70.

The magnifying lens 132b is for magnifying and observing the eye to be examined 6.

The wide-angle lens 132a and the magnifying lens 132b are each held by the holding plate 132c that is connected to the distal end of the arm 134. The wide-angle lens 132a and the magnifying lens 132b are each fixedly disposed at both ends of the holding plate 132c having a longitudinal direction. The holding plate 132c has the center portion rotatably connected to the distal end of the arm 134. By rotating the holding plate 132c, the user can select whether the lens to be placed in front of the eye to be examined 6 is the wide-angle lens 132a or the magnifying lens 132b in a manner that depends on situations. Switching between the wide-angle lens 132a and the magnifying lens 132b by a rotational movement of the holding plate 132c may be manually performed or may be automatically performed.

As shown in FIGS. 1 and 7, the arm 134 supports the front optical system 130.

The arm 134 includes a first link 134a, a second link 134c, and a joint portion 134b. The arm 134 is foldable.

The first link 134a and the second link 134c are connected via the joint portion 134b. The first link 134a and the second link 134c are configured such that the positional relationship between the first link 134a and the second link 134c is variable through the joint portion 134b.

An end portion of the first link 134a, which is opposite to the end portion at which the joint portion 134b is positioned, is coupled to the joining unit 133. The first link 134a is configured such that the positional relationship between the first link 134a and the joining unit 133 is variable.

An end portion of the second link 134c, which is opposite to the end portion at which the joint portion 134b is positioned, corresponds to the distal end of the arm 134. The holding plate 132c is connected to the end portion of the second link 134c. The positional relationship between the second link 134c and the holding plate 132c is configured to be variable.

The movement of the arm 134 can change the positions of the reduction lens 131, the wide-angle lens 132a, and the magnifying lens 132b. The movement of the arm 134 can locate the wide-angle lens 132a (or the magnifying lens 132b) on or off the observation optical path.

In this manner, the movement of the arm 134 and the holding plate 132c can change the positions of the reduction lens 131, the wide-angle lens 132a, and the magnifying lens 132b.

The arm driving unit 135 is constituted by an actuator that is provided in the joint portion 134b and drives the arm 134. The arm driving unit 135 is controlled on the basis of a microscope control signal generated by the CCU 20.

[Main Functions of Ophthalmic Microscope System]

Next, main functions of the microscope system 100 will be described using a main functional block diagram of the microscope system 100 shown in FIG. 3.

(Main Functions of Microscope)

Figure 3:
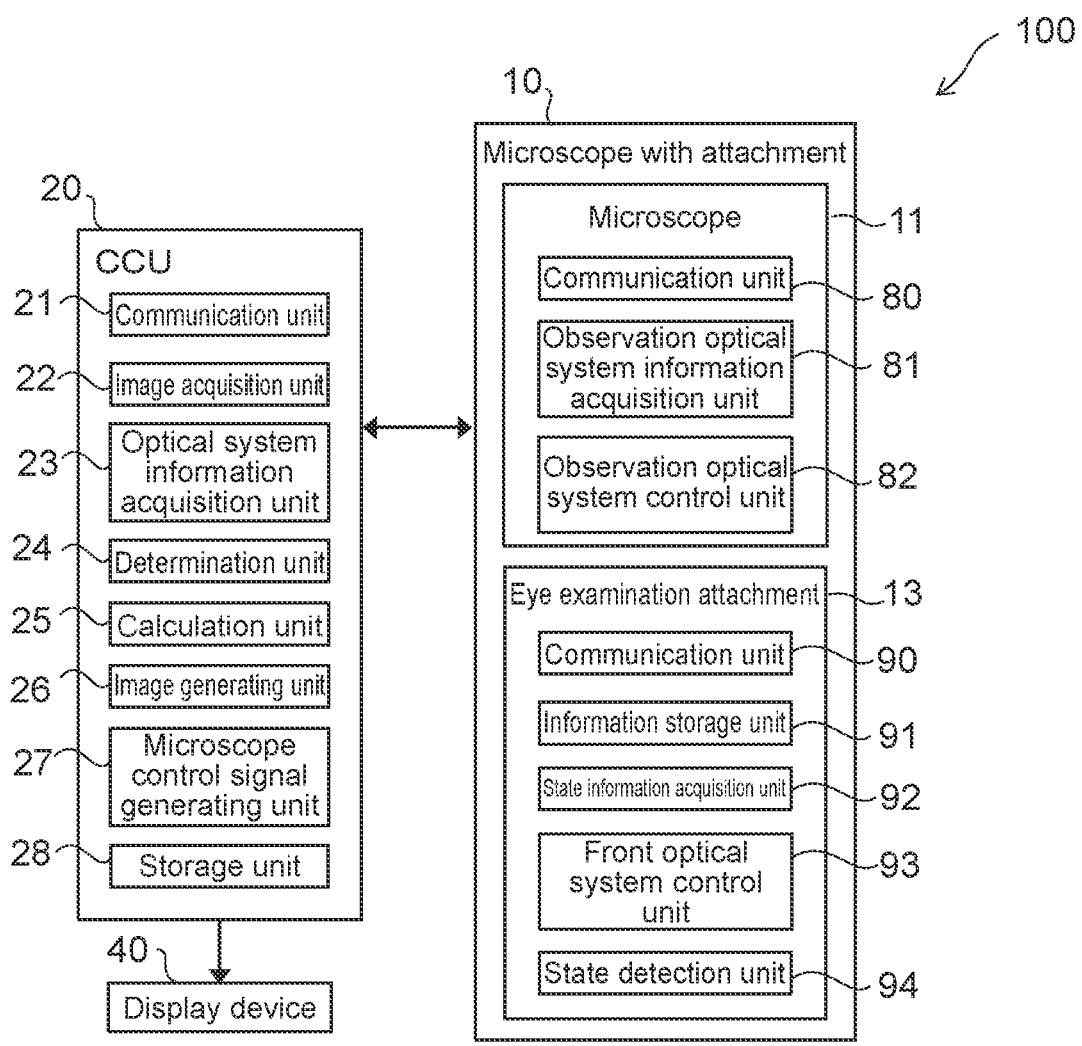
FIG. 3 A functional block diagram showing main functions of the ophthalmic microscope system.

As shown in FIG. 3, the microscope 11 includes a communication unit 80, an observation optical system information acquisition unit 81 and an observation optical system control unit 82 that controls the observation optical system 17.

The communication unit 80 communicates with an external device such as the CCU 20 wirelessly or with a wire.

The communication unit 80 sends a captured image captured by the image pickup element 181 to the CCU 20. Moreover, the communication unit 80 receives a microscope control signal generated by the CCU 20.

The observation optical system information acquisition unit 81 acquires state information of the observation optical system 17.

The state information of the observation optical system 17 includes focal position information that is changed depending on the position of the focusing device 171, magnification (angle of view) information that changes the position of each lens in the variable magnification lens system 172 including a plurality of zoom lenses, F-value information for changing the opening state of the variable aperture 173 that adjusts the amount of light entering through the lens, and the like. It can also be said that the focal position information is the position information of the focusing device 171. It can also be said that the magnification (angle of view) information is the position information of each lens in the variable magnification lens system 172. It can also be said that the F-value information is opening state information of the variable aperture 173.

The observation optical system control unit 82 controls the observation optical system 17.

More specifically, the observation optical system control unit 82 controls the focusing device 171, the variable magnification lens system, and the variable aperture 173, based on a microscope control signal generated by the CCU 20 on the basis of information regarding the front optical system 130.

(Main Functions of Eye Examination Attachment)

The eye examination attachment 13 includes a communication unit 90, an information storage unit 91, a state information acquisition unit 92, a front optical system control unit 93, and a state detection unit 94.

The communication unit 90 communicates with the external device such as the CCU 20 wirelessly or with a wire.

The communication unit 90 sends the optical characteristic information of the front optical system 130 stored in the information storage unit 91 to the CCU 20. Moreover, the communication unit 90 receives a microscope control signal generated by the CCU 20. Moreover, the communication unit 90 sends information indicating the joining state to the CCU 20 in a case where the joining between the microscope 11 and the eye examination attachment 13 is detected.

It should be noted that in this embodiment, a configuration in which the communication unit 90 of the eye examination attachment 13 and a communication unit 21 of the CCU 20, which will be described later, directly communicate with each other will be taken as an example, though not limited thereto. For example, there may be employed a configuration in which the communication unit 90 of the eye examination attachment 13 and the communication unit 80 of the microscope 11 are capable of communicating with each other and the communication unit 90 of the eye examination attachment 13 and the communication unit 21 of the CCU 20 communicate with each other via the communication unit 80 of the microscope 11.

The information storage unit 91 prestores the optical characteristic information of the front optical system 130.

The optical characteristic information of the front optical system 130 includes at least one of the functional characteristic information of the front lens (the wide-angle lens 132a or the magnifying lens 132b), a shape of the front lens, or a material of the front lens.

The functional characteristic information includes at least one of the focal distance, the distortion coefficient, the refractive index, the wavelength characteristic, the polarization characteristic, a numerical aperture (NA), or the depth of field of each of the wide-angle lens 132a and the magnifying lens 132b serving as the front lenses.

In this embodiment, the example in which the information storage unit 91 stores the specific optical characteristic information of the front optical system 130 has been taken, though not limited thereto.

For example, an identification (ID) different may be added to each of different types of front optical systems and the information storage unit 91 may store this ID as the optical characteristic information. In this case, the ID of the front optical system and the specific optical characteristic information of the front optical system associated with the ID may be stored in a database of a server that is an external device (not shown). After the CCU 20 acquires the ID from the microscope 10 with the attachment via the communication unit 21, the specific optical characteristic information of the front optical system associated with the ID is acquired from the database of the server.

Alternatively, IDs each added to different types of front optical systems in advance and specific optical characteristic information associated with the IDs may be stored not in the database of the server but in a storage unit 28 of the CCU 20 to be described later. Based on an ID acquired from the microscope 10 with the attachment, the CCU 20 acquires from the storage unit 28 the specific optical characteristic information of the front optical system associated with the ID.

The configuration in which an ID different for each type of front optical system is added, and, using this ID, the specific optical characteristic information of the front optical system is acquired from the external device or by the CCU may be employed as described above.

The state information acquisition unit 92 acquires state information of the front optical system 130.

The state information includes the position information of each of the reduction lens 131, the wide-angle lens 132a, and the magnifying lens 132b. The position information of each lens can be detected through an encoder (not shown), for example. The state information may include distance information between the lenses, direction information of each lens which depends on switching between the wide-angle lens 132a and the magnifying lens 132b, and the like. The state information is information that is changed depending on the movement of the arm 134 or the holding plate 132c.

The distance information between the lenses is a distance between the wide-angle lens 132a or the magnifying lens 132b and the reduction lens 131, for example. It should be noted that the distance between the lenses may be calculated by using the position information of each lens.

The direction information of the lens is switching information between the wide-angle lens 132a and the magnifying lens 132b that can be placed in front of the eye to be examined 6, and is information related to the direction of the lens with respect to the eye to be examined 6. For example, in a case where the wide-angle lens 132a is placed in front of the eye to be examined 6, direction information indicating that the wide-angle lens 132a is located in front of the eye to be examined 6 and the magnifying lens 132b is not located in front of the eye to be examined 6. In other words, the lens switching information is rotation information of the holding plate 132c.

The front optical system control unit 93 controls the front optical system 130. More specifically, the front optical system control unit 93 controls the arm driving unit 135, based on a microscope control signal generated by the CCU 20 on the basis of information regarding the front optical system 130. Accordingly, the arm 134 can drive to change the positions of the reduction lens 131, the wide-angle lens 132a, and the magnifying lens 132b. Thus, the distance between the reduction lens 131 and the wide-angle lens 132a (or the magnifying lens 132b) can be changed.

The state detection unit 94 detects connection/disconnection between the eye examination attachment 13 and the microscope 11 on the basis of whether or not electrical conduction at the contact point provided in the portion in which the eye examination attachment 13 and the microscope 11 are brought into contact with each other is achieved.

Moreover, the state detection unit 94 detects a mechanical change in the front optical system 130, for example, the movement of the arm 134 or the movement of the holding plate 132c.

The information detected by the state detection unit 94 is sent to the CCU 20.

(Main Functions of CCU)

The CCU 20 includes the communication unit 21, an image acquisition unit 22, an optical system information acquisition unit 23, a determination unit 24, a calculation unit 25, an image generating unit 26, a microscope control signal generating unit 27, and the storage unit 28.

The communication unit 21 communicates with external devices such as the display device 40, the microscope 11 of the microscope 10 with the attachment, and the eye examination attachment 13 wirelessly or with a wire.

The communication unit 21 receives the information regarding the front optical system 130 from the eye examination attachment 13, for example.

Moreover, the communication unit 21 receives, from the eye examination attachment 13, information detected by the state detection unit 94. The communication unit 21 receives information indicating that the microscope 11 and the eye examination attachment 13 are in the joining state and information regarding whether or not a mechanical change in the front optical system 130 is performed as the information detected by the state detection unit 94.

The communication unit 21 receives from the microscope 11 the state information of the observation optical system 17. The communication unit 21 also receives a captured image from the microscope 11.

The communication unit 21 sends to the microscope 11 and the eye examination attachment 13 a microscope control signal generated using the information of the front optical system 130.

The communication unit 21, the communication unit 80, and the communication unit 90 may each have a configuration to perform wired communication via a communication cable, for example, or may each have a configuration to perform wireless communication such as Wi-Fi, Bluetooth (registered trademark), and near-field communication (NFC).

The image acquisition unit 22 acquires the captured image captured by the image pickup element 181, from the microscope 11 via the communication unit 21.

The optical system information acquisition unit 23 acquires information regarding the optical system of the microscope 10 with the attachment via the communication unit 21.

The information regarding the optical system of the microscope 10 with the attachment includes the optical characteristic information of the front optical system 130 and information regarding the optical system through which the return light (the image of the eye to be examined) passes before the return light (the image of the eye to be examined) from the eye to be examined 6 is formed as an image on the image pickup element 181.

The information regarding the optical system through which the return light passes before the return light is formed as an image on the image pickup element 181 includes the state information of the front optical system 130 and the state information of the observation optical system 17.

The optical characteristic information and the state information of the front optical system 130, which are the information regarding the front optical system 130, are acquired from the eye examination attachment 13.

The optical characteristic information of the front optical system 130 is information prestored in an information storage unit 137 of the eye examination attachment 13. The optical system information acquisition unit 23 acquires the optical characteristic information of the front optical system 130 that is stored in the information storage unit 137.

The state information of the front optical system 130 is information acquired by the state information acquisition unit 92 of the eye examination attachment 13. The optical system information acquisition unit 23 acquires the state information of the front optical system 130 that is acquired by the state information acquisition unit 92.

The optical system information acquisition unit 23 acquires the state information of the observation optical system 17 that is acquired by the observation optical system information acquisition unit 81 of the microscope 11.

Based on the detection result of the state detection unit 94, the determination unit 24 determines whether or not the eye examination attachment 13 and the microscope 11 are joined to each other. The determination unit 24 determines that the eye examination attachment 13 and the microscope 11 are joined with each other in a case where the communication unit 21 receives a detection result indicating that the state detection unit 94 has detected the joining between the microscope 11 and the eye examination attachment 13. The determination unit 24 determines that the eye examination attachment 13 and the microscope 11 are not joined with each other in a case where the communication unit 21 does not receive a detection result indicating that the state detection unit 94 has detected the joining between the microscope 11 and the eye examination attachment 13.

In addition, the determination unit 24 determines whether or not the state of the front optical system 130 changes on the basis of the detection result of the state detection unit 94. In a case where the communication unit 21 receives a detection result indicating that the state detection unit 94 has detected the state change of the front optical system 130, the determination unit 24 determines that the state of the front optical system 130 is changed. In a case where the communication unit 21 does not receive a detection result indicating that the state detection unit 94 has detected the state change of the front optical system 130, the determination unit 24 determines that the state of the front optical system 130 is not changed.

As described above, whether or not the state of the front optical system 130 is changed may be determined on the basis of a physical movement change inside the eye examination attachment 13. Alternatively, whether or not the state of the front optical system 130 is changed may be determined by image recognition using the captured image obtained by imaging.

The state change of the front optical system 130 includes, for example, switching between the wide-angle lens 132a and the magnifying lens 132b according to the rotational movement of the holding plate 132c. In addition, the state change of the front optical system 130 includes, for example, a change in distance between the reduction lens 131 and the wide-angle lens 132a (or the magnifying lens 132b) located on the observation optical path due to the movement of the arm 134, and the like.

It should be here noted that the example in which the determination unit 24 determines whether or not the state of the front optical system 130 changes on the basis of detection results of the movement of the arm 134 and the movement of the holding plate 132c according to the state detection unit 94 has been taken, though not limited thereto.

For example, in a case where the position information detected by an encoder of each of the reduction lens 131, the wide-angle lens 132a, and the magnifying lens 132b changes, it may be determined that the state of the front optical system 130 is changed.

The calculation unit 25 uses the information regarding the optical system of the microscope 10 with the attachment acquired by the optical system information acquisition unit 23 to thereby calculate a correction parameter for correcting the captured image and the focal position of the optical system before the return light of the microscope 10 with the attachment from the eye to be examined 6 is formed as an image on the image pickup element 181. Moreover, a magnification suitable for the display image is calculated.

The calculation unit 25 calculates the correction parameter as follows, for example, in a state in which the eye examination attachment 13 is joined to the microscope 11 and the front lens such as the wide-angle lens 132a and the magnifying lens 132b is located in front of the eye to be examined 6.

That is, the calculation unit 25 calculates a distortion correction parameter such that a distortion of the captured image due to the placement of the wide-angle lens 132a is corrected by using a distortion coefficient of the wide-angle lens 132a as the optical characteristic information of the front optical system 130, for example.

Moreover, the calculation unit 25 calculates a focal position and a magnification as follows in a state in which the eye examination attachment 13 is joined to the microscope 11 and the front lens such as the wide-angle lens 132a and the magnifying lens 132b is located in front of the eye to be examined 6.

That is, the calculation unit 25 calculates a focal position to adjust the relative positional relationship among the objective lens 15, the front lens (the wide-angle lens 132a or the magnifying lens 132b), and the eye to be examined 6 such that the position of the focal point on the back side of the front lens (the wide-angle lens 132a or the magnifying lens 132b) coincides with the position of the focal point on the front side of the objective lens 15 and the focus is set on the fundus 67, and also calculates a magnification.

The image generating unit 26 corrects the captured image on the basis of the correction parameter calculated by the calculation unit 25, generates a display image by performing image processing such as color enhancement in a manner that depends on needs, and outputs the display image to the display device 40 via the communication unit 21.

The microscope control signal generating unit 27 generates a microscope control signal on the basis of the calculation results of the magnification and the focal position calculated by the calculation unit 25 and outputs the microscope control signal to the microscope 10 with the attachment via the communication unit 21. The microscope control signal includes at least one of a control signal associated with the control on the observation optical system 17 of the microscope 11 or a control signal associated with the control on the front optical system 130 of the eye examination attachment 13.

The storage unit 28 stores the information acquired by the optical system information acquisition unit 23 in time series. Moreover, the storage unit 28 stores the distortion correction parameter, the focal position, and the magnification that are calculated by the calculation unit 25.

[Operation of CCU]

Next, an operation of the CCU 20 of the microscope system 100 will be described.

Hereinafter, in a first embodiment, the description will be given taking an example in which the wide-angle lens 132a is located on the observation optical path and a display image is generated by performing image correction using a distortion coefficient of the wide-angle lens that is the optical characteristic information of the front optical system 130.

In a second embodiment, an example in which a microscope control signal is generated using the state information of the front optical system 130 will be described.

First Embodiment

Figure 8:
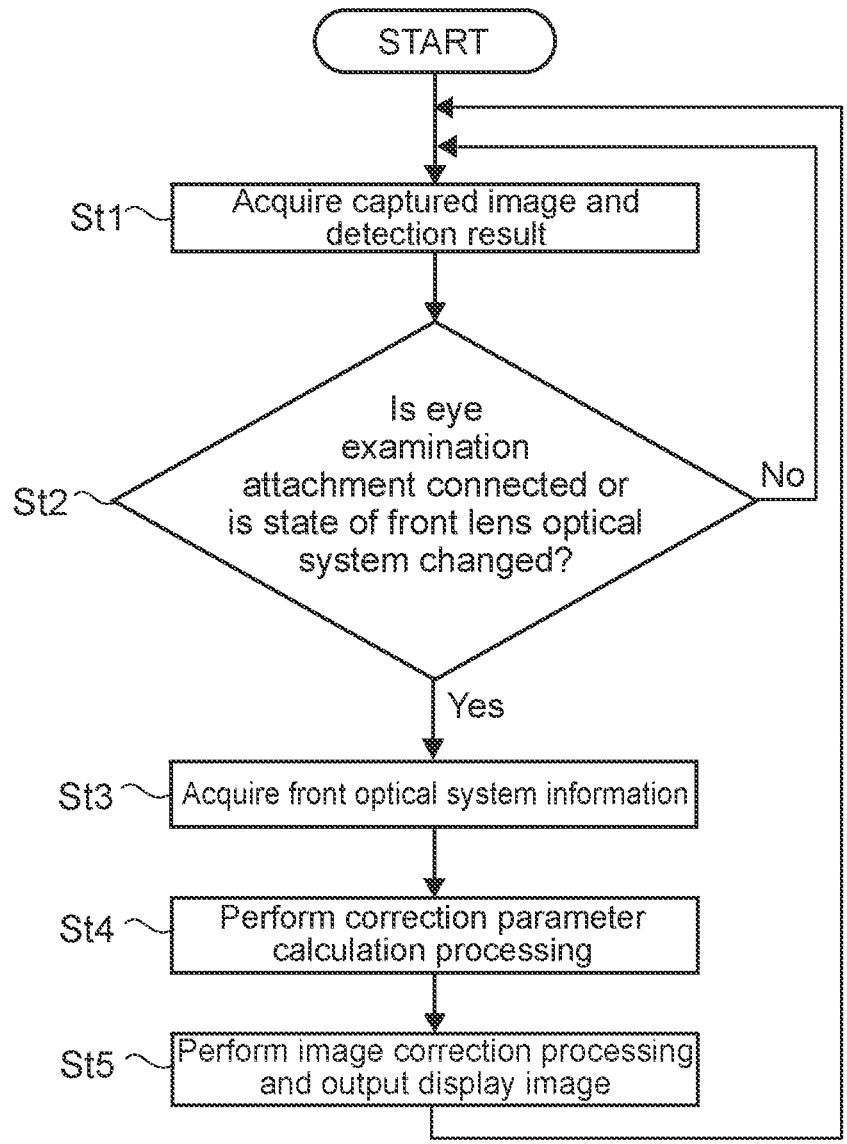
FIG. 8 A flowchart showing an operation of a CCU according to a first embodiment.

FIG. 8 is a flowchart showing the operation of the CCU 20.

Figure 9A:
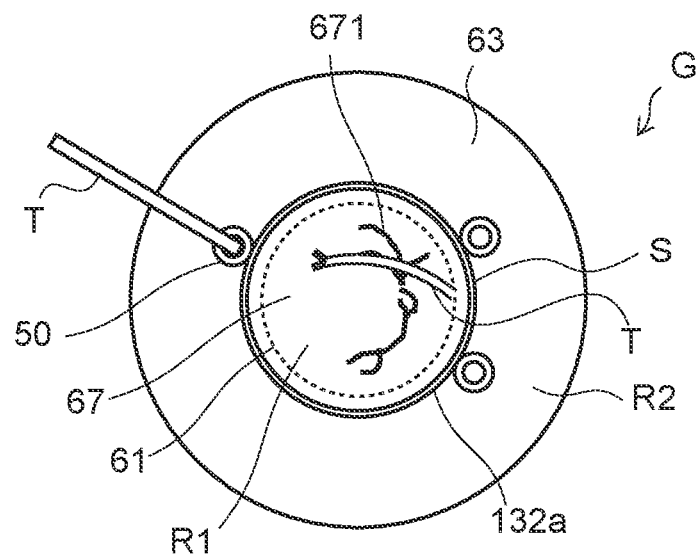
FIGS. 9A, 9B, and 9C A diagram for describing each of images of the eye to be examined before inversion processing and image correction processing using optical system information of an eye examination attachment, after the image correction processing is performed, and after both the inversion processing and the image correction processing are performed.
Figure 9B:
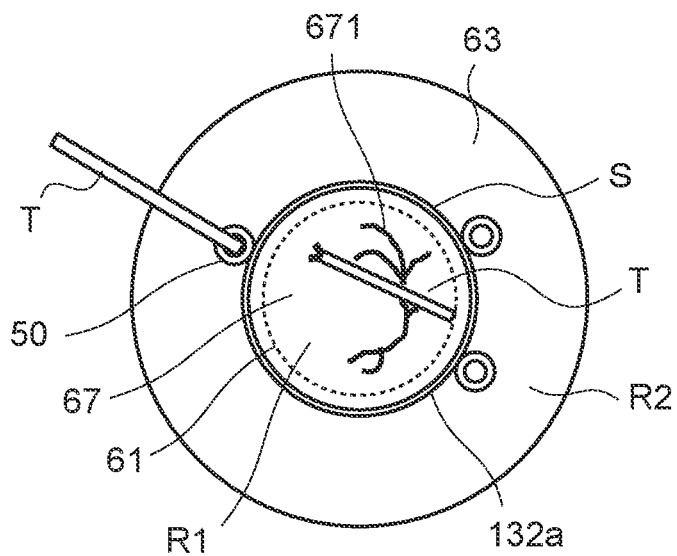
Figure 9C:
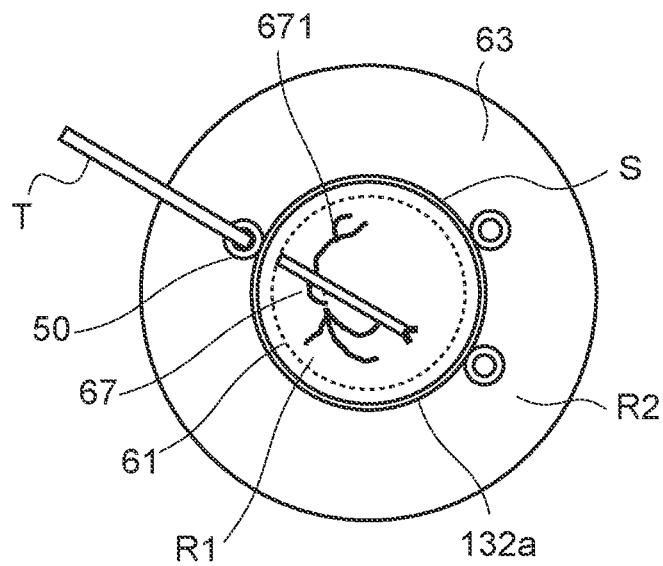

FIGS. 9A, 9B, and 9C are diagrams for describing image correction processing using the optical characteristic information of the front optical system 130.

FIG. 9A is a schematic diagram showing a captured image of an eye to be examined on which inversion processing and distortion correction processing are not performed.

FIG. 9B is a schematic diagram showing a display image on which the inversion processing is not performed and the distortion correction processing is performed.

FIG. 9C is a schematic diagram showing a display image on which the inversion processing and the distortion correction processing are not performed.

Hereinafter, the description will be given in accordance with the flow of FIG. 8 and, as necessary, using FIGS. 9A, 9B, and 9C.

As shown in FIG. 8, the communication unit 21 acquires from the microscope 10 with the attachment a captured image captured by the image pickup element 181 and a detection result detected by the state detection unit 94 (St1). The captured image is output to the image acquisition unit 22. The detection result is output to the determination unit 24.

Here, a captured image G will be described with reference to FIG. 9A. As shown in FIG. 9A, as to the captured image G, a region inside a rim S of the wide-angle lens 132a is an inversion region R1 in which the image is inverted when the wide-angle lens 132a is placed in front of the eye to be examined 6. The inversion region R1 is a region in which the image is formed through the wide-angle lens 132a serving as the front lens. In FIGS. 9A, 9B, and 9C, a region in which the image is inverted is shown as a non-inversion region R2.

Moreover, as to the captured image G, distortion is caused by the wide-angle lens 132a in the inversion region R1, and the captured image G is an image in which the surgical instrument T, which has a linear shape in the real world, is curved as shown in FIG. 9A.

Next, based on a detection result received by the communication unit 21, the determination unit 24 determines whether or not the eye examination attachment 13 and the microscope 11 are joined to each other or, in a case where the eye examination attachment 13 is already joined to the microscope 11, whether or not the state of the front optical system 130 is changed (St2).

In a case where the determination unit 24 determines that the eye examination attachment 13 and the microscope 11 are joined to each other or that the state of the front optical system 130 is changed (YES), the processing proceeds to St3.

On the other hand, in a case where the determination unit 24 determines that the eye examination attachment 13 and the microscope 11 are not joined to each other or that the state of the front optical system 130 is not changed (NO), the processing returns to St1 and then the processing is performed again.

In St3, the optical system information acquisition unit 23 acquires the information regarding the front optical system 130 and the state information of the observation optical system 17.

In this embodiment, the distortion coefficient (the optical characteristic information of the front optical system) of the wide-angle lens 132a (or the magnifying lens 132b) serving as the front lens and the state information of the front optical system 130 are acquired as the information regarding the front optical system 130. The magnification (angle of view) information of the observation optical system 17 is acquired as the state information of the observation optical system 17.

The storage unit 28 stores, in time series, the information acquired by the optical system information acquisition unit 23.

Next, using the distortion coefficient of the wide-angle lens 132a (or the magnifying lens 132b), the state information of the front optical system 130, and the magnification (angle of view) information of the observation optical system 17, the calculation unit 25 calculates a distortion correction parameter for correcting the distortion in the captured image (St4), the distortion being caused by the use of the wide-angle lens 132a. The magnification information of the observation optical system 17 is used for calculating a range in the captured image, in which the distortion correction is to be applied.

Here, also in a case where it is determined that the state of the front optical system 130 is changed, the distortion correction parameter is calculated again and anew.

The calculated distortion correction parameter is stored in the storage unit 28.

Next, the image generating unit 26 performs distortion correction processing of the captured image by using the distortion correction parameter calculated by the calculation unit 25, performs correction processing such as enhancement processing as necessary, and outputs a display image generated through the image processing to the display device 40 (St5).

In the display device 40, the display image generated by the image generating unit 26 is displayed.

In the image corrected by the distortion correction processing, the distortion of the region of the inversion region R1 is reduced as shown in FIG. 9B, and the shape of the surgical instrument T in the image becomes linear similar to the surgical instrument T in the real world.

In addition, the inverted image correction inverter 14 performs inversion processing of changing the inverted image of the inversion region R1 into the normal image.

Through the inversion processing performed by the inverted image correction inverter 14, the inverted image of the inversion region R1 due to the presence of the wide-angle lens changes into the normal image while the image of the non-inversion region R2 that is a region not having the inverted image due to the absence of the wide-angle lens is inverted. The image generating unit 26 performs inversion correction processing on the non-inversion region R2 having the image inverted by the inverted image correction inverter 14 so as to change the inverted image into the normal image.

Next, the image generating unit 26 combines the inversion region R1 having the normal image through the inversion processing of the inverted image correction inverter 14 with the non-inversion region R2 subjected to the inversion correction processing. As a result, a display image that does not make the user feel discomfort is generated as shown in FIG. 9C.

The inversion processing performed by the inverted image correction inverter 14 may be configured to perform the inversion processing performed by the inverted image correction inverter 14 in a case where the state detection unit 94 detects the joining between the eye examination attachment 13 and the microscope 11, for example.

It should be noted that although the example in which the inversion processing is performed after the distortion correction processing is shown here, this order is not limited. The distortion correction processing may be performed after the inversion processing or the distortion correction processing may be performed at the same time of the inversion processing, though not limited thereto.

In this manner, the processing shown in FIG. 8 is repeated.

In this embodiment, also in a case where the state of the front optical system 130 is changed, the distortion correction processing suitable for the state of the optical system of the microscope 10 with the attachment at that time is performed on the captured image. Therefore, the user can perform surgery while observing a constantly suitable display image.

Moreover, the example in which the display image is generated by performing the distortion correction processing on the captured image with the distortion coefficient of the front lens as the optical characteristic information of the front optical system 130 has been taken in this embodiment, though not limited thereto.

For example, the display image may be generated by controlling the maximum magnification of the digital zoom, using the material information of the front lens as the optical characteristic information of the front optical system 130.

Here, for zooming the display image, there are an optically zooming method performed by controlling the observation optical system 17 and a zooming method (digital zoom) performed by image processing of the captured image.

The front lens is made of plastic, glass, and the like, for example. Since the resolution of the lens such as modulation transfer function (MTF) varies depending on the material of the front lens, the maximum magnification of the digital zoom may be controlled using the material of the front lens to prevent magnification beyond the resolution of the front lens.

Moreover, on the basis of information indicating that the front optical system 130 has a polarization characteristic as the optical characteristic information of the front optical system 130, the display image may be generated by performing specular reflection removal of removing, by a well-known method, specular reflection components from a polarization image (captured image) captured by the image pickup element. Through the specular reflection removal, room light and the like reflected on the lens are removed. Thus, a suitable display image can be presented to the user and a more safe treatment using an image with reduced specular reflection can be expected.

Moreover, the display image may be generated by performing the color aberration correction on the captured image, using shape information of a lens that constitutes the front optical system 130 as the optical characteristic information of the front optical system 130.

Moreover, in a case of a configuration with which a stereo image is obtained, the display image may be generated by controlling the parallax of the stereo image, using the focal distance of the front optical system 130 as the optical characteristic information of the front optical system 130.

In the above-mentioned manner, the display image can be obtained by performing image processing on the captured image with the optical characteristic information of the front optical system 130. It should be noted that it is sufficient that such image processing using the optical characteristic information of the front optical system 130 is performed at least one time.

Moreover, although the example in which the distortion correction processing is automatically performed using the distortion coefficient has been taken, a configuration to enable the user to select whether or not to perform the distortion correction processing may be employed.

For example, in a case where a touch panel is provided as the input device 41 on the display screen of the display device 40 and the eye examination attachment 13 and the microscope 11 are joined to each other, a menu button for selecting whether or not to perform the distortion correction processing may be displayed on the display screen so as to enable the user to select whether or not to perform the distortion correction processing.

As still another example, in a case where the front optical system 130 has a polarization characteristic, a menu button for selecting whether or not to perform the specular reflection removal may be displayed on the display screen to enable the user to select whether or not to perform the specular reflection removal.

As described above, in the microscope system 100, the eye examination attachment 13 has the optical characteristic information of the front optical system in advance, and thus a display image appropriate to a situation can be provided to the user by using this optical characteristic information.

Moreover, in the microscope system 100, even when a state change of the front optical system 130, for example, a position change of the front lens or the reduction lens due to a movement of the arm 134 or the holding plate 132*c* occurs, image processing is performed using the information regarding the optical system of the microscope 10 with the attachment. In this way, a display image or observation image appropriate to a situation can be provided to the user.

Second Embodiment

Next, an example in which the microscope system 100 generates a microscope control signal by using optical characteristic information of the front optical system 130 and controls the microscope 10 with the attachment by using this microscope control signal will be described.

Here, joining the eye examination attachment 13 to the microscope 11 changes a position at which an image is formed, and thus it is necessary to adjust the optical system of the microscope 10 with the attachment.

In this embodiment, a microscope control signal for controlling the optical system through which return light from the optical system of the microscope 10 with the attachment, more specifically, the eye to be examined 6 passes before the return light is formed as an image on the image pickup element 181 is generated using the optical characteristic information of the front optical system 130, and the optical system of the microscope 10 with the attachment is automatically adjusted on the basis of this microscope control signal.

Hereinafter, the description will be given with reference to FIG. 10.

Figure 10:
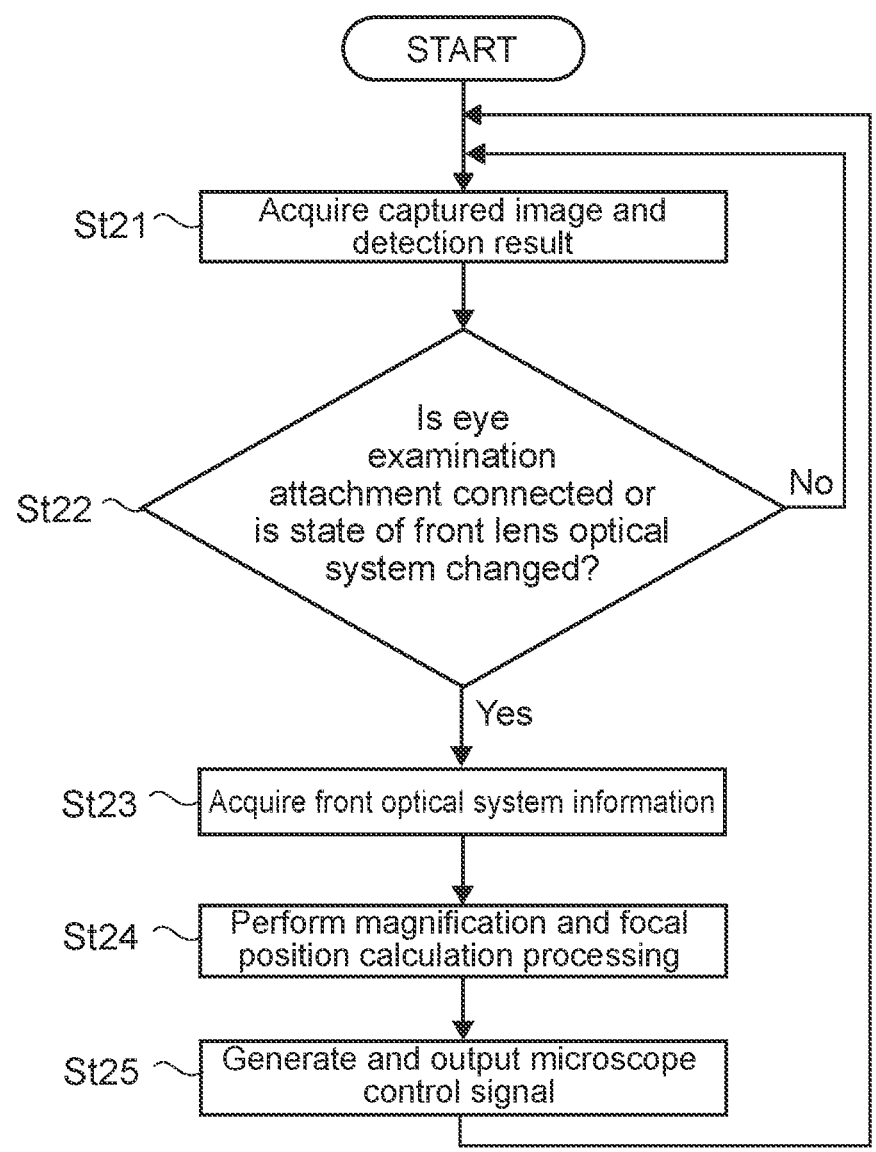
FIG. 10 A flowchart showing an operation of a CCU according to a second embodiment.

FIG. 10 is a flowchart showing the operation of the CCU 20.

As shown in FIG. 10, the communication unit 21 acquires from the microscope 10 with the attachment a captured image captured by the image pickup element 181 and a detection result detected by the state detection unit 94 (St21). The captured image is output to the image acquisition unit 22. The detection result is output to the determination unit 24.

Next, based on a detection result received by the communication unit 21, the determination unit 24 determines whether or not the eye examination attachment 13 and the microscope 11 are joined to each other, or in a case where the eye examination attachment 13 is already joined to the microscope 11, whether or not the state of the front optical system 130 is changed (St22).

In a case where the determination unit 24 determines that the eye examination attachment 13 and the microscope 11 are joined to each other or that the state of the front optical system 130 is changed (YES), the processing proceeds to St23.

On the other hand, in a case where the determination unit 24 determines that the eye examination attachment 13 and the microscope 11 are not joined with each other or that the state of the front optical system 130 is not changed (NO), the processing returns to St21 and then the processing is performed again.

In St23, the optical system information acquisition unit 23 acquires information regarding the front optical system 130 and state information of the observation optical system 17 as the optical system information.

In this embodiment, the focal distance (the optical characteristic information) of the wide-angle lens 132a (or the magnifying lens 132b) serving as the front lens and the state information of the front optical system 130 are acquired as the information regarding the front optical system 130. The state information of the front optical system 130 is position information of each lens. Moreover, information regarding a magnification (angle of view), a focal position, an F-value, and the like of the observation optical system 17 is acquired as the state information of the observation optical system 17.

The storage unit 28 stores, in time series, the information acquired by the optical system information acquisition unit 23.

Next, the calculation unit 25 calculates a focal position and a magnification of the optical system through which return light from the eye to be examined 6 passes before the return light is formed as an image on the image pickup element 181, using the state information of the front optical system 130, the state information of the observation optical system 17, and the focal distance of the wide-angle lens 132a (or the magnifying lens 132b).

That is, the calculation unit 25 calculates a focal position to adjust the relative positional relationship among the objective lens 15, the front lens (the wide-angle lens 132a or the magnifying lens 132b), and the eye to be examined 6 such that the position of the focal point on the back side of the front lens (the wide-angle lens 132a or the magnifying lens 132b) coincides with the position of the focal point on the front side of the objective lens 15 and the focus is set on the fundus 67. The calculation unit 25 also calculates a magnification suitable for the display image.

The storage unit 28 stores the calculated focal position and magnification.

Next, the microscope control signal generating unit 27 generates, on the basis of the calculated focal position and magnification, a microscope control signal for controlling each of the focusing device 171 and the variable magnification lens system 172 of the microscope 11 and outputs the microscope control signal to the microscope 10 with the attachment (St25).

In this manner, the processing shown in FIG. 10 is repeated.

In the microscope 11, the observation optical system control unit 82 controls driving of the focusing device 171 and the variable magnification lens system 172 on the basis of a microscope control signal generated by the CCU 20.

Accordingly, the focal position and the magnification of the optical system of the microscope 10 with the attachment, to which the eye examination attachment 13 is joined, are automatically adjusted. Thus, the image of the eye to be examined 6 observed through the front lens can be observed with a suitable display image.

It should be here noted that the example in which the observation optical system 17 is controlled has been taken, though a configuration in which the front optical system 130 is controlled and the magnification and the focal position are adjusted may be employed. In this case, a microscope control signal for driving the arm driving unit 135 of the eye examination attachment 13 is generated and output in St25.

Moreover, a configuration to control both the observation optical system 17 and the front optical system 130 may be employed. In this case, a microscope control signal for controlling driving of the focusing device 171 and the variable magnification lens system 172 and a microscope control signal for driving the arm driving unit 135 are generated and output in St25.

Tunable lenses (variable focal length lenses) whose lens shape (e.g., lens curvature) changes in accordance with electrical control such as pressure application through a magnetic actuator may be used as the reduction lens 131 and the front lens (the wide-angle lens 132a or the magnifying lens 132b) that constitute the front optical system 130.

In a case where the tunable lenses are used, a microscope control signal is generated using the optical characteristic information of the tunable lens (the optical characteristic information of the front optical system) and the state information of the front optical system 130 and the state information of the observation optical system 17 that are acquired from the microscope 10 with the attachment. This microscope control signal is a signal for changing the lens shapes of the reduction lens and the front lens, which are the tunable lenses, such that the position of the focal point on the back side of the front lens coincides with the position of the focal point on the front side of the objective lens 15 and the focus is set on the fundus 67. Moreover, the optical characteristic information of the tunable lens includes a focal distance range, a lens distortion coefficient, a lens shape, and the like, which the tunable lenses can have and which are associated with each other.

Moreover, besides the control of the focal position and the magnification (the angle of view), a configuration to control the variable aperture 173 of the observation optical system 17 by using information regarding the numerical aperture (NA) or the depth of field of the front optical system as the optical characteristic information of the front optical system 130 may be employed.

For example, the variable aperture 173 is controlled such that the depth of field of the observation optical system 17 increases when the depth of field of the front optical system 130 is small.

As in this embodiment, in a case where the optical system of the microscope is automatically adjusted using the information regarding the front optical system, the display device and the image pickup element are not essential and the present technology can also be applied to an ophthalmic microscope system for performing observation and surgery by user's eyepiece observation with a microscope without using a display device. Also in this system, the user can observe the image of the eye to be examined 6 observed through the front lens with a suitable observation image.

As described above, the optical system through which return light from the eye to be examined 6 passes before the return light is formed as an image on the image pickup element 181 is controlled using the optical characteristic information of the front optical system that the eye examination attachment 13 has in advance. Thus, a display image or observation image of the eye to be examined 6, which is suitable for a situation after the focal position is adjusted, can be provided to the user.

Moreover, in this embodiment, the user is released from the troublesome work of adjusting the optical system of the microscope 10 with the attachment due to the joining of the eye examination attachment 13. As described above, in the microscope system 100 according to this embodiment, the eye examination attachment 13 including the front optical system 130 has the optical characteristic information of the front optical system 130, and thus the user's microscope setting work can be supported.

Moreover, in the microscope system 100 according to this embodiment, even when the state of the front optical system 130, for example, the position of the front lens or the reduction lens is changed due to the movement of the arm 134 or the holding plate 132*c*, the microscope is controlled using the information regarding the optical system of the microscope 10 with the attachment. Thus, a display image or observation image whose focal position is appropriate and which is suitable for a situation can be provided to the user constantly.

The embodiments of the present technology are not limited to the above-mentioned embodiments, and various modifications can be made without departing from the gist of the present technology.

For example, in the above-mentioned embodiments, for the sake of easy understanding, the image correction processing and the microscope control signal generation processing using the optical characteristic information of the front optical system have been separately described in the different embodiments, though both the processing may be performed.

Moreover, for example, the example in which the inversion processing is performed by using the inverted image correction inverter 14 has been taken in the above-mentioned embodiments, though not limited thereto. For example, the inversion processing may be performed by performing image processing on the captured image acquired by the image pickup element 181 and it will be described with reference to FIG. 9.

FIG. 9A is a schematic diagram showing the image of an eye to be examined on which the inversion processing and the distortion correction processing are not performed.

FIG. 9C is a schematic diagram showing a display image on which the inversion processing and the distortion correction processing are performed.

As shown in FIG. 9A, in the captured image on which the distortion correction processing is not performed, the surgical instrument T is shown in a greatly curved form due to the interposition of the wide-angle lens 132*a*.

In a manner similar to that described above, the distortion correction of the captured image G is performed using the distortion coefficient of the wide-angle lens 132*a* that is the optical characteristic information of the front optical system and the inversion processing is also performed by the image processing. Thus, as shown in FIG. 9C, the display image in which the image of the surgical instrument T is linear and the inversion region R1 is subjected to the inversion processing is obtained.

In the inversion processing by the image processing, an inverted region detector (not shown) provided in the CCU 20 first detects the inversion region R1 in the captured image G.

Detection of the inversion region R1 can be performed using object recognition. Alternatively, the inversion region R1 may be detected by using the fact that the outside of the front lens (the wide-angle lens 132*a* or the magnifying lens 132*b*) is a region (white 63 of the eye) corresponding to a sclera while the inside of the front lens 132 is a region (cornea) having color and texture different from those of the white of the eye, such as an iris and a pupil.

Alternatively, it is also possible to perform edge detection processing and detect the region inside the detected edge as the inversion region R1 because there is a clear edge at the peripheral edge S of the front lens in the captured image.

The above-mentioned detection methods detect the inversion region R1 from the single captured image.

Moreover, in a case where the image pickup element 181 is mounted on each of the right and left sides of the microscope 10 with the attachment, captured images for both the left eye and the right eye can be obtained. Depth information may be extracted from parallax information of the two captured images and the inversion region R1 may be detected by using the fact that the front lens is placed in front of the eye.

Alternatively, the inversion region R1 may be detected using a plurality of captured images. Specifically, a captured image when the front lens is not mounted may be held, the captured image may be compared with a captured image including the front lens, and a region having a large difference therebetween may be detected as the inversion region R1.

The range of the detected inversion region R1 is supplied to the image processing unit 25.

The image generating unit 26 inverts the inversion region R1 included in the captured image G output from the image pickup element 181 to be point-symmetric about the center of the inversion region R1. In addition, the image generating unit 26 combines the inversion region R1 and the non-inversion region R2 by matching the outer periphery of the inverted inversion region R1 and the inner periphery of the non-inversion region R2.

Accordingly, the image generating unit 26 is capable of generating a display image in which the inversion is cancelled as shown in FIG. 9C. The image generating unit 26 outputs the generated display image to the display device 40 for displaying the generated display image on the display device 40.

As described above, the inversion processing may be performed by the image processing to generate the display image, and the user can perform observation and treatment of the eye to be examined 6 while viewing the display image displayed on the display device 40.

Moreover, although the wide-angle lens for observing the fundus has been exemplified in the above-mentioned embodiments, for example, the gonio lens may be used. The use of the gonio lens can observe an angle of an eye. In a case of using the gonio lens, the gonio lens is used in contact with the eye to be examined 6. In a case of the angle observation, intraocular illumination and the reduction lens become unnecessary.

Moreover, although the eye examination attachment 13 is configured to include the two front lenses that are the wide-angle lens 132*a* and the magnifying lens 132*b* in the above-mentioned embodiments, for example, the eye examination attachment 13 is configured to include a single front lens.

Moreover, for example, in the above-mentioned embodiments, the wide-angle lens 132*a* and the magnifying lens 132*b* may be each configured to be detachable from the holding plate 132*c*. In this case, the type of front lens to be used can be changed to an arbitrary one.

Alternatively, the holding plate 132*c* may be configured to be detachable from the arm 134. Also in this case, the type of front lens to be used can be changed to an arbitrary one.

In a case where the front lens is detachable as such, when a different type of front lens is newly mounted for example, the information storage unit 91 of the eye examination attachment 13 may be configured such that optical characteristic information and the ID of the newly mounted front lens are writable therein. Accordingly, an eye examination attachment excellent in customizing property and extensibility can be realized without the need for modifying the microscope 11.

It should be noted that the present technology may take the following configurations.

(1) An eye examination attachment, including:
a joining unit capable of being joined to an ophthalmic microscope;
a front optical system including a front lens capable of being placed in front of an eye to be examined; and
a communication unit that sends information regarding the front optical system to an external device.

(2) The eye examination attachment according to (1), further including
a storage unit that stores optical characteristic information of the front optical system as the information regarding the front optical system.

(3) The eye examination attachment according to (2), in which
the optical characteristic information of the front optical system includes at least one of functional characteristic information of the front lens, a shape of the front lens, or a material of the front lens.

(4) The eye examination attachment according to (3), in which
the functional characteristic information includes at least one of a focal distance, a distortion coefficient, a refractive index, a wavelength characteristic, or a polarization characteristic of the front lens.

(5) The eye examination attachment according to any one of (1) to (4), further including
a state information acquisition unit that acquires state information of the optical system as the information regarding the front optical system.

(6) The eye examination attachment according to (5), in which
the state information of the front optical system includes position information of the front lens.

(7) The eye examination attachment according to (6), in which
the front optical system includes the front lens and an intermediate lens that is placed between the front lens and the ophthalmic microscope, and
the state information of the front optical system further includes at least one of position information of the intermediate lens or distance information between the intermediate lens and the front lens.

(8) The eye examination attachment according to (2), in which
the front lens is configured to be replaceable, and
the storage unit is configured such that the optical characteristic information of the front optical system is writable on the storage unit.

(9) The eye examination attachment according to any one of (1) to (8), further including
a front optical system control unit that controls the front optical system on the basis of a control signal from the external device.

(10) A control device, including
a communication unit that receives information regarding a front optical system of an eye examination attachment including the front optical system including a front lens capable of being placed in front of an eye to be examined.

(11) The control device according to (10), further including:
an image acquisition unit that acquires a captured image of an eye to be examined in front of which the front lens is placed; and
an image generating unit that generates a display image by performing image processing on the captured image with the information regarding the front optical system.

(12) The control device according to (11), in which
the eye examination attachment further includes a storage unit that stores optical characteristic information of the front optical system as the information regarding the front optical system.

(13) The control device according to (11) or (12), in which
the information regarding the front optical system includes a distortion coefficient of the front lens, and
the image generating unit generates the display image by performing distortion correction on the captured image with the distortion coefficient.

(14) The control device according to (11) or (12), in which
the information regarding the front optical system includes a material of the front lens, and
the image generating unit generates the display image by controlling a maximum magnification on the basis of the material of the lens.

(15) The control device according to (11) or (12), in which
the information regarding the front optical system includes a polarization characteristic of the front lens, and
the image generating unit generates the display image by performing specular reflection removal on the captured image on the basis of the polarization characteristic of the front lens.

(16) The control device according to (11) or (12), in which
the information regarding the front optical system includes a shape of the front lens, and
the image generating unit generates the display image by performing color aberration correction on the captured image with shape information of the front lens.

(17) The control device according to (11) or (12), in which
the captured image is a stereo image,
the information regarding the front optical system includes a focal distance of the front lens, and
the image generating unit generates the display image by controlling a parallax of the stereo image with the focal distance of the front lens.

(18) The control device according to any one of (10) to (17), in which
the eye examination attachment is configured to be capable of being joined to an ophthalmic microscope including an observation optical system, further including
a microscope control signal generating unit that generates a control signal for controlling at least one of the observation optical system or the front optical system, using the information regarding the front optical system.

(19) An ophthalmic microscope system, including:
an ophthalmic microscope;
an eye examination attachment including
a joining unit that is joined to the ophthalmic microscope,
a front optical system including a front lens capable of being placed in front of an eye to be examined, and
a communication unit that sends information regarding the front optical system; and
a control device including a communication unit that receives the information regarding the front optical system.

(20) The ophthalmic microscope system according to (19), in which
the ophthalmic microscope further includes an image pickup element, and
the control device further includes
an image acquisition unit that acquires a captured image of an eye to be examined in front of which the front lens is placed, the eye to be examined being imaged by the image pickup element, and
an image generating unit that generates a display image by performing image processing on the captured image with the information regarding the front optical system.
(21) The ophthalmic microscope system according to (19) or (20), in which
the ophthalmic microscope further includes an observation optical system, and
the control device further includes a microscope control signal generating unit that generates a control signal for controlling at least one of the observation optical system or the front optical system, using the information regarding the front optical system.

REFERENCE SIGNS LIST 6 eye to be examined
11 ophthalmic microscope
13 eye examination attachment
17 observation optical system
20 CCU (control device, external device)
21 communication unit
22 image acquisition unit
26 image generating unit
27 microscope control signal generating unit
90 communication unit
91 information storage unit (storage unit)
93 front optical system control unit
100 ophthalmic microscope system
130 front optical system
131 reduction lens (intermediate lens)
132a wide-angle lens (front lens)
132b magnifying lens (front lens)
133 joining unit
181 image pickup element

The invention claimed is:

1. An eye examination attachment, comprising:
a joining unit configured to join with an ophthalmic microscope;
a front optical system coupled to the joining unit, wherein the front optical system includes a front lens configured for placement in front of an eye; and
a communication unit configured to send information regarding the front optical system to an external device.

2. The eye examination attachment according to claim 1, further comprising a storage unit configured to store optical characteristic information of the front optical system, wherein the information regarding the front optical system includes the optical characteristic information.

3. The eye examination attachment according to claim 2, wherein
the front lens is configured to be replaceable, and
the optical characteristic information of the front optical system is writable on the storage unit.

4. The eye examination attachment according to claim 2, wherein the optical characteristic information of the front optical system includes at least one of functional characteristic information of the front lens, a shape of the front lens, or a material of the front lens.

5. The eye examination attachment according to claim 4, wherein the functional characteristic information includes at least one of a focal distance, a distortion coefficient, a refractive index, a wavelength characteristic, or a polarization characteristic of the front lens.

6. The eye examination attachment according to claim 1, further comprising a state information acquisition unit configured to acquire state information of the front optical system, wherein the information regarding the front optical system includes the state information.

7. The eye examination attachment according to claim 6, wherein the state information of the front optical system includes position information of the front lens.

8. The eye examination attachment according to claim 7, wherein
the front optical system further includes an intermediate lens between the front lens and the ophthalmic microscope, and
the state information of the front optical system further includes at least one of position information of the intermediate lens or distance information between the intermediate lens and the front lens.

9. The eye examination attachment according to claim 1, further comprising a front optical system control unit configured to control the front optical system based on a control signal from the external device.

10. A control device, comprising:
a communication unit configured to receive information regarding a front optical system of an eye examination attachment, wherein
the front optical system includes a front lens configured for placement in front of an eye to be examined,
the eye examination attachment configured to join with an ophthalmic microscope, and
the ophthalmic microscope includes an observation optical system; and
a microscope control signal generating unit configured to generate a control signal based on the information regarding the front optical system, wherein the control signal controls at least one of the observation optical system or the front optical system.

11. The control device according to claim 10, further comprising:
an image acquisition unit configured to acquire a captured image of the eye; and
an image generating unit configured to:
perform image processing on the captured image based on the information regarding the front optical system; and
generate a display image based on the image processing on the captured image.

12. The control device according to claim 11, wherein
the eye examination attachment further includes a storage unit configured to store optical characteristic information of the front optical system, and
the information regarding the front optical system includes the optical characteristic information.

13. The control device according to claim 12, wherein
the information regarding the front optical system includes a distortion coefficient of the front lens, and
the image generating unit is further configured to perform, based on the distortion coefficient of the front lens, distortion correction on the captured image, wherein the display image is generated based on the distortion correction performed on the captured image.

14. The control device according to claim 12, wherein
the information regarding the front optical system includes a material of the front lens, and
the image generating unit is further configured to control a magnification based on the material of the front lens, wherein the display image is generated based on the controlled magnification.

15. The control device according to claim 12, wherein
the information regarding the front optical system includes a polarization characteristic of the front lens, and
the image generating unit is further configured to perform specular reflection removal on the captured image based on the polarization characteristic of the front lens, wherein the display image is generated based on the specular reflection removal performed on the captured image.

16. The control device according to claim 12, wherein
the information regarding the front optical system includes a shape of the front lens, and
the image generating unit is further configured to perform color aberration correction on the captured image based on the shape of the front lens, wherein the display image is generated based on the color aberration correction performed on the captured image.

17. The control device according to claim 12, wherein
the captured image is a stereo image,
the information regarding the front optical system includes a focal distance of the front lens, and
the image generating unit is further configured to control a parallax of the stereo image based on the focal distance of the front lens, wherein the display image is generated based on the controlled parallax of the stereo image.

18. An ophthalmic microscope system, comprising:
an ophthalmic microscope;
an eye examination attachment including:
  a joining unit configured to join with the ophthalmic microscope;
  a front optical system coupled to the joining unit, wherein the front optical system includes a front lens configured for placement in front of an eye; and
  a first communication unit configured to send information regarding the front optical system to an external device; and
a control device including a second communication unit, wherein the second communication unit is configured to receive the information regarding the front optical system.

19. The ophthalmic microscope system according to claim 18, wherein
the ophthalmic microscope further includes an image pickup element, wherein the image pickup element is configured to capture an image of the eye, and
the control device further includes:
  an image acquisition unit configured to acquire the captured image of the eye; and
  an image generating unit configured to:
    perform image processing on the captured image based on the front optical system; and
    generate a display image based on the image processing performed on the captured image.

20. The ophthalmic microscope system according to claim 18, wherein
the ophthalmic microscope further includes an observation optical system, and
the control device further includes a microscope control signal generating unit configured to generate a control signal based on the information regarding the front optical system, wherein the control signal controls at least one of the observation optical system or the front optical system.

21. The eye examination attachment according to claim 18, wherein
the information regarding the front optical system includes a distortion coefficient of the front lens, and
the control device further comprising:
  an image acquisition unit configured to acquire a captured image of the eye; and
  an image generating unit configured to correct, based on the distortion coefficient of the front lens, distortion of the captured image.

* * * * *